United States Patent
Nam et al.

(10) Patent No.: US 11,420,924 B2
(45) Date of Patent: Aug. 23, 2022

(54) METHOD FOR PURIFYING ORGANIC ACIDS

(71) Applicant: LG CHEM, LTD., Seoul (KR)

(72) Inventors: Hyun Nam, Daejeon (KR); Kyung Moo Lee, Daejeon (KR); Yukyung Lim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 43 days.

(21) Appl. No.: 16/976,049

(22) PCT Filed: Oct. 4, 2019

(86) PCT No.: PCT/KR2019/013000
§ 371 (c)(1),
(2) Date: Aug. 26, 2020

(87) PCT Pub. No.: WO2020/080713
PCT Pub. Date: Apr. 23, 2020

(65) Prior Publication Data
US 2021/0363092 A1    Nov. 25, 2021

(30) Foreign Application Priority Data
Oct. 17, 2018   (KR) .................. 10-2018-0123888

(51) Int. Cl.
| C07C 51/48 | (2006.01) |
| B01D 11/04 | (2006.01) |
| B01D 3/10 | (2006.01) |
| C12P 7/42 | (2006.01) |

(52) U.S. Cl.
CPC ............ C07C 51/48 (2013.01); B01D 3/10 (2013.01); B01D 11/0484 (2013.01); B01D 11/0488 (2013.01); B01D 11/0492 (2013.01); C12P 7/42 (2013.01)

(58) Field of Classification Search
CPC ........ C07C 51/48; C07C 53/122; C12P 7/42; B01D 11/0488; B01D 11/0492; B01D 3/10
See application file for complete search history.

(56) References Cited

U.S. PATENT DOCUMENTS

| 6,229,046 | B1 | 5/2001 | Eyal et al. |
| 6,320,077 | B1 | 11/2001 | Eyal et al. |
| 6,534,679 | B2 | 3/2003 | Eyal et al. |
| 7,144,977 | B2 | 12/2006 | Eyal et al. |
| 8,703,451 | B2 | 4/2014 | Haas et al. |
| 8,859,808 | B2 | 10/2014 | Yoshida |
| 2003/0176736 | A1 | 9/2003 | Eyal et al. |
| 2005/0256337 | A1 | 11/2005 | Verser et al. |
| 2010/0187472 | A1 | 7/2010 | Verser et al. |
| 2012/0112127 | A1 | 5/2012 | Verser et al. |
| 2013/0011886 | A1* | 1/2013 | Tolan ................ C12P 7/10 435/126 |
| 2013/0245320 | A1* | 9/2013 | Yoshida ............ C07C 51/42 562/580 |

FOREIGN PATENT DOCUMENTS

| JP | 2007-082490 A | 4/2007 | |
| JP | 2007-522136 A | 8/2007 | |
| JP | 2008-035732 A | 2/2008 | |
| JP | 2011-148740 A | 8/2011 | |
| JP | 2011148740 A * | 8/2011 | ............ C07C 51/48 |
| JP | 2013-537541 A | 10/2013 | |
| JP | 2014-187989 A | 10/2014 | |
| KR | 10-0598188 B1 | 7/2006 | |
| KR | 20110081518 A * | 7/2011 | ............... C12P 7/00 |
| KR | 10-2014-0096787 A | 8/2014 | |
| KR | 10-1664450 B1 | 10/2016 | |

OTHER PUBLICATIONS

KR 20110081518 (A), (KR 101664450 (B), Chang Ho Nam et al., Method for preparing volatile fatty acids from biomass, English translation, 26 pages (Year: 2011).*
JP 2011148740 (A), Kobayashi Osamu et al., Method for recovering organic acid in water, English translation, 16 pages (Year: 2011).*
Burge, et al. (2016.).Reactive extraction of bio-based 3-hydroxypropionic acid assisted by hollow-fiber membrane contactor using TOA and Aliquat 336 in n-decanol.J Chem Technol Biotechnol. Society of Chemical Industry. vol. 91, pp. 2705-2712.
Sadaka, et al. (1998).The Effect of Temperature on Forward/Back Extraction Using an Amine Extractant for the Recovery of Cyclic Hydroxy Carboxylic Acids. Separation Science and Technology. 33(11), pp. 1667-1680.

* cited by examiner

Primary Examiner — Yate' K Cutliff
(74) Attorney, Agent, or Firm — Dentons US LLP

(57) ABSTRACT

Provided is a method for purifying organic acids, including: a first extraction which includes separating an aqueous solution of organic acids into a first organic layer and a first aqueous solution layer by adding a solvent containing an amine and an alcohol; removing the alcohol from the separated first organic layer; and a second extraction which includes separating the first organic layer from which the alcohol has been removed into a second organic layer and a second aqueous solution layer by adding water.

12 Claims, No Drawings

METHOD FOR PURIFYING ORGANIC ACIDS

CROSS-REFERENCE TO RELATED APPLICATIONS

This application is a National Stage Application of International Application No. PCT/KR2019/013000 filed on Oct. 4, 2019, which claims priority to Korean Patent Application No. 10-2018-0123888 filed on Oct. 17, 2018 with the Korean Intellectual Property Office, the disclosure of which is incorporated herein by reference in its entirety.

TECHNICAL FIELD

The present disclosure relates to a method for purifying organic acids, which improves an extraction efficiency and effectively recovers the organic acid at a high concentration from a low-concentration aqueous solution of organic acids.

BACKGROUND 3-hydroxypropionic acid (3-HP), an organic acid, is a synthetic intermediate that can be used in various chemical processes, and is an industrially important compound used as a raw material for the synthesis of various compounds such as high value-added 1,3-propanediol, acrylic acid, methyl acrylate, acrylamide, ethyl 3-hydroxypropionate, malonic acid, propiolactone, and acrylonitrile.

These organic acids can also be produced by a pure chemical process, but recently, they are produced by separating and purifying a low concentration (<10 wt %) culture medium obtained in a microorganism-based fermentation process. For such separation and purification, a liquid-liquid extraction technique or a reaction extraction technique is generally used instead of an energy-intensive water evaporation method.

In order to recover the organic acid at a high concentration from a low-concentration aqueous solution of organic acids produced by a fermentation process, a two-step extraction process should be applied. A method of first extracting an organic acid contained in an aqueous solution using an organic solvent as a first step, and then back-extracting (secondary extraction) using water has been used to purify the organic acid.

However, when using this two-step extraction process, there is a problem that an efficiency of the secondary extraction using water is very poor, because the organic solvent used in the primary extraction and the organic acid forms a stable complex.

Therefore, recovering organic acids at a high concentration from a low-concentration aqueous solution of organic acids produced by microbial fermentation is a long-standing problem in the field to which the present invention belongs, and there is a need to develop an economical purification process capable of continuously and effectively separating and purifying low-concentration organic acids from a microbial fermentation broth.

DETAILED DESCRIPTION OF THE INVENTION

Technical Problem

The present disclosure is to provide a method for purifying organic acids, which effectively recovers the organic acid at a high concentration from a low-concentration aqueous solution of organic acids.

Technical Solution

In the present disclosure, there is provided a method for purifying organic acids, including:

a first extraction step of separating an aqueous solution of organic acids into a first organic layer and a first aqueous solution layer by adding a solvent containing an amine and an alcohol;

a step of removing the alcohol from the separated first organic layer; and a second extraction step of separating the first organic layer from which the alcohol has been removed into a second organic layer and a second aqueous solution layer by adding water.

Hereinafter, a method for purifying organic acids according to a specific embodiment of the present invention will be described in more detail.

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, numbers, steps, components, or combinations thereof, but do not preclude the presence or addition of one or more other features, numbers, steps, components, or combinations thereof.

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

According to the present disclosure, there can be provided a method for purifying organic acids, including:

a first extraction step of separating an aqueous solution of organic acids into a first organic layer and a first aqueous solution layer by adding a solvent containing an amine and an alcohol;

a step of removing the alcohol from the separated first organic layer; and a second extraction step of separating the first organic layer from which the alcohol has been removed into a second organic layer and a second aqueous solution layer by adding water.

The present inventors have confirmed through experiments that a method for purifying organic acids including a first extraction step of separating an aqueous solution of organic acids into a first organic layer and a first aqueous solution layer by adding a solvent containing an amine and an alcohol; a step of removing the alcohol from the separated first organic layer; and a second extraction step of separating the first organic layer from which the alcohol has been removed into a second organic layer and a second aqueous solution layer by adding water can effectively recover the organic acid at a high concentration from a low-concentration aqueous solution of organic acids by maximizing an extraction efficiency. And, the present invention has been completed on the basis of such findings.

Specifically, they have confirmed through experiments that when an amine and an alcohol are included as extraction solvents in the first extraction step, the alcohol functions as a component of the extraction solvent, thereby increasing a first extraction efficiency by stabilizing a complex formed by the combination of the organic acid and the amine. Also, they have confirmed that the removal of the alcohol before the second extraction changes the state of the stable complex to also increase a second extraction efficiency, thereby effectively obtaining the organic acid at a high concentration.

At this time, the aqueous solution of organic acids can be a fermentation broth obtained in a microorganism-based fermentation process, or can be an aqueous solution containing an organic acid having 2 to 10 carbon atoms containing a hydroxy group.

Meanwhile, the organic acid having 2 to 10 carbon atoms containing a hydroxy group can be included at a concentration of 3 to 10% in the aqueous solution of organic acids. When the concentration of the organic acid having 2 to 10 carbon atoms containing a hydroxy group is less than 3%, the method may not be economical due to the use of excessive extraction solvent or an increase in extraction time.

The organic acid having 2 to 10 carbon atoms containing a hydroxy group can be at least one selected from the group consisting of glycolic acid, 3-hydroxypropionic acid, lactic acid or 10-hydroxydecanoic acid. Preferably, it can be 3-hydroxypropionic acid.

Meanwhile, as the extraction solvent used for extracting the organic acid in the first extraction step, a solvent containing both an amine and an alcohol can be used.

When the solvent containing an amine and an alcohol is added to the aqueous solution of organic acids, the organic acid contained in the aqueous solution of organic acids is dissolved in the solvent, and the solvent and water are separated into a first organic layer and a first aqueous solution layer.

At this time, a volume ratio of the aqueous solution of organic acids and the solvent containing an amine and an alcohol can be 1:0.5 to 1:1.5 in the first extraction step. When the first extraction is performed within the above volume ratio, the extraction efficiency can be increased while minimizing the amount of the extraction solvent used, thereby having an optimal effect in the first extraction efficiency. When the volume ratio of the aqueous solution of organic acids and the solvent containing an amine and an alcohol is less than 1:0.5, there is a concern that the extraction efficiency can be lowered because the amount of the extraction solvent used is small. When it exceeds 1:1.5, the extraction efficiency is increased, but the amount of alcohol to be removed afterwards can be increased, resulting in an increase in energy cost.

Meanwhile, a weight ratio of the amine and the alcohol in the extraction solvent can be 15:85 to 45:55. When the weight ratio of the amine is less than 15%, the amine content is insufficient, and thus the formation of the complex is not smooth, resulting in a decrease in extraction efficiency. Moreover, the alcohol content is relatively large, so that the amount of energy required to remove the alcohol can be increased. On the other hand, when the amine content is 45% or more, the extraction efficiency may not increase any more.

The amine is not particularly limited, and for example, can be at least one amine selected from the group consisting of tri-n-octylamine, tridecylamine or Aliquat 336. Preferably, it can be tri-n-octylamine.

In addition, the alcohol is not particularly limited, and for example, can be at least one alcohol selected from the group consisting of 1-hexanol, 1-heptanol, and 1-octanol. Preferably, it can be 1-hexanol.

The first extraction step can be carried out at a temperature of 0 to 50° C., and preferably at a temperature of 20 to 30° C.

When the temperature of the first extraction is less than 0° C., coagulation of the first aqueous solution layer can occur, and when it exceeds 50° C., the reaction extraction efficiency can be lowered.

In addition, stirring in the first extraction step can be carried out at 500 to 700 rpm for 7 to 17 hours.

After the first extraction step of separating the aqueous solution of organic acids into the first organic layer and the first aqueous solution layer by adding a solvent containing an amine and an alcohol, a step of removing the alcohol from the separated first organic layer can be performed.

As mentioned above, the removal of the alcohol changes the state of the stable complex formed by the combination of the organic acid and the amine, so that the organic acid can be more smoothly extracted into the second aqueous solution layer in the second extraction step, thereby increasing the second extraction efficiency and effectively obtaining the organic acid at a high concentration.

At this time, the method for removing the alcohol is not particularly limited, but can be performed, for example, by distillation. However, in order to prevent deformation of the organic acid in the distillation process, it is most preferable to apply vacuum distillation.

After the step of removing the alcohol from the separated first organic layer, a second extraction step of separating the first organic layer from which the alcohol has been removed into a second organic layer and a second aqueous solution layer by adding water can be performed.

When water is added to the first organic layer from which the alcohol has been removed, the organic acid contained in the first organic layer is dissolved in water, and the solvent and water are separated into a second organic layer and a second aqueous solution layer.

The second extraction step can be carried out at a temperature of 50 to 100° C., and preferably at a temperature of 70 to 90° C.

When the temperature of the second extraction is less than 50° C., the extraction efficiency can be lowered, and when it exceeds 100° C., evaporation of water, which is an extraction solvent, occurs.

In addition, stirring in the second extraction step can be carried out at 500 to 700 rpm for 5 to 7 hours.

As described above, the organic acid can be effectively purified from the low-concentration aqueous solution of organic acids at a high concentration through the first extraction step, the removal of alcohol, and the second extraction step.

According to the embodiment to be described later, when removing the alcohol before the second extraction step as described above, the extraction efficiency of the second extraction step was increased by about twice or more compared to the purification without removing the alcohol. In addition, it was confirmed that a ratio of the concentration of the organic acid contained in the second aqueous solution layer to the concentration of the organic acid contained in the second organic layer was also increased by about twice or more.

According to the above purification method, the removal of the alcohol changes the state of the stable complex formed by the combination of the organic acid and the amine, so that the organic acid can be more smoothly extracted into the second aqueous solution layer in the second extraction step, thereby increasing the second extraction efficiency.

ADVANTAGEOUS EFFECTS

In the present disclosure, there is provided a method for purifying organic acids, which effectively recovers the organic acid at a high concentration from a low-concentration aqueous solution of organic acids.

DETAILED DESCRIPTION

The present invention will be described in more detail with reference to the following examples. However, these examples are for illustrative purposes only, and the invention is not intended to be limited by these examples.

Experimental Example 1

Examples 1 to 5

In the first extraction step, the first extraction efficiency was analyzed by varying the type and content of the extraction solvent with respect to the aqueous solution of organic acids.

The aqueous solution of organic acids contains 7.2 wt % of 3-hydroxypropionic acid as a fermentation broth obtained in a microorganism-based fermentation process. For extraction, tri-n-octylamine (TOA) and Aliquat 336 were used as the amine, and 1-hexanol was used as the alcohol.

After adding the alcohol and amine shown in Table 1 to the aqueous solution of organic acids and stirring at a constant temperature for a certain period of time, it was allowed to stand and separated into a first organic layer and a first aqueous solution layer to perform a first extraction.

Then, the content of the organic acid contained in the separated first organic layer was analyzed using HPLC, and the result is shown in Table 1 below.

Comparative Example 1

After adding the alcohol and amine in the amounts shown in Table 1 to the aqueous solution of organic acids containing 7.2 wt % of 3-hydroxypropionic acid and stirring at 30° C. for 7 hours, it was allowed to stand and separated into a first organic layer and a first aqueous solution layer to perform a first extraction.

Then, the content of the organic acid contained in the separated first organic layer was analyzed using HPLC, and the result is shown in Table 1 below.

TABLE 1

| | Aqueous solution of organic acids (g) | Solvent | | | | Aqueous solution of organic acids:solvent (volume ratio) | Reaction temp. (° C.) | Stirring time (hr) | 1st extraction efficiency (%) |
| | | Amine | | Alcohol | | | | | |
| | | Type | Amount (g) | Type | Amount (g) | | | | |
|---|---|---|---|---|---|---|---|---|---|
| Example 1 | 51.0 | TOA | 12.4 | Hexanol | 29.2 | 1:1.0 | 30 | 7 | 66.8 |
| Example 2 | 51.0 | TOA Aliquat 336 | 9.3 10.2 | Hexanol | 23.0 | 1:1.0 | 20 | 15 | 60.2 |
| Example 3 | 51.0 | TOA | 9.3 | Hexanol | 11.5 | 1:0.5 | 20 | 17 | 52.1 |
| Example 4 | 51.0 | TOA | 18.6 | Hexanol | 23.0 | 1:1.0 | 20 | 17 | 70.3 |
| Example 5 | 51.0 | TOA | 27.9 | Hexanol | 34.5 | 1:1.5 | 20 | 17 | 82.6 |
| Comp. Example 1 | 51.3 | TOA | 12.4 | Dodecanol | 29.2 | 1:1.0 | 30 | 7 | 50.3 |

Referring to Table 1, it was confirmed that Examples 1 to 5, in which the volume ratio of the aqueous solution of organic acids and the solvent containing an amine and an alcohol is 1:0.5 to 1:1.5, had a first extraction efficiency of 52.1% or more in the purification of the aqueous solution of 3-hydroxypropionic acid.

Experimental Example 2

Examples 4, 6 and 7

In the first extraction step, the total amount of the extraction solvent was kept the same, and the first extraction efficiency was analyzed while changing the ratio of amine and alcohol.

After adding the amine and alcohol in the amounts shown in Table 2 to the aqueous solution of organic acids containing 7.2 wt % of 3-hydroxypropionic acid and stirring at 20° C. for 17 hours, it was allowed to stand and separated into a first organic layer and a first aqueous solution layer to perform a first extraction.

Then, the content of the organic acid contained in the separated first organic layer was measured using HPLC to analyze the extraction efficiency of the first extraction step, and the result is shown in Table 2 below.

TABLE 2

| | Aqueous solution of organic acids (g) | Solvent Amine | | Solvent Alcohol | | Amine:alcohol (weight ratio) | 1st extraction efficiency (%) |
|---|---|---|---|---|---|---|---|
| | | Type | Amount (g) | Type | Amount (g) | | |
| Example 6 | 51.0 | TOA | 6.2 | Hexanol | 35.4 | 15:85 | 45.8 |
| Example 7 | 51.0 | TOA | 12.4 | Hexanol | 29.2 | 30:70 | 71.4 |
| Example 4 | 51.0 | TOA | 18.6 | Hexanol | 23.0 | 45:55 | 70.3 |

Referring to Table 2, it was confirmed that Examples 4, 6, and 7, in which the weight ratio of amine and alcohol is 15:85 to 45:55 in the solvent, had a first extraction efficiency of 45.8% or more in the purification of the aqueous solution of 3-hydroxypropionic acid.

Experimental Example 3

Examples 4, 5, 8 to 10

After adding the amine and alcohol in the amounts shown in Table 3 to the aqueous solution of organic acids containing 7.2 wt % of 3-hydroxypropionic acid and stirring at 20° C. for 17 hours, it was allowed to stand and separated into a first organic layer and a first aqueous solution layer to perform a first extraction.

Thereafter, 1-hexanol in the separated first organic layer was removed by vacuum distillation at 70° C., and water was added to the first organic layer from which the alcohol was removed, followed by stirring at 90° C. for 7 hours. Then, it was allowed to stand and separated into a second organic layer and a second aqueous solution layer to perform a second extraction.

Then, the content of the organic acid contained in the separated second aqueous solution layer was measured using HPLC to analyze the extraction efficiency of the second extraction step, and the result is shown in Table 3 below.

Comparative Example 2

After adding the amine and alcohol in the amounts shown in Table 3 to the aqueous solution of organic acids containing 7.2 wt % of 3-hydroxypropionic acid and stirring at 20° C. for 17 hours, it was allowed to stand and separated into a first organic layer and a first aqueous solution layer to perform a first extraction.

At this time, the volume ratio of the aqueous solution of organic acids and the solvent containing the amine and alcohol was 1:1.0, and the weight ratio of the amine and alcohol in the solvent was 30:70.

After adding water to the separated first organic layer and stirring at 90° C. for 7 hours, it was allowed to stand and separated into a second organic layer and a second aqueous solution layer to perform a second extraction.

Then, the content of the organic acid contained in the separated second aqueous solution layer was measured using HPLC to analyze the extraction efficiency of the second extraction step, and the result is shown in Table 3 below.

TABLE 3

| | 1st extraction | | | | 2nd extraction | | | |
|---|---|---|---|---|---|---|---|---|
| | Aqueous solution of organic acids (g) | TOA (g) | Hexanol (g) | Removal of alcohol | 2nd organic layer (g) | 2nd aqueous solution layer (g) | 2nd extraction efficiency (%) | Partition coefficient |
| Example 4 | 51.0 | 18.6 | 23.0 | ○ | 26.0 | 9.0 | 55.3 | 3.691 |
| Example 5 | 51.0 | 27.9 | 34.5 | ○ | 41.1 | 20.0 | 69.5 | 4.635 |
| Example 8 | 82.2 | 30.0 | 37.1 | ○ | 11.0 | 5.5 | 68.6 | 5.281 |
| Example 9 | 82.2 | 30.0 | 37.1 | ○ | 11.0 | 11.0 | 81.9 | 5.065 |
| Example 10 | 82.2 | 30.0 | 37.1 | ○ | 11.0 | 16.5 | 82.4 | 3.387 |
| Comp. Example 2 | 51.0 | 12.4 | 29.2 | X | 49.8 | 25.0 | 30.8 | 0.853 |

The partition coefficient refers to a ratio of the concentration of the organic acid contained in the second aqueous solution layer to the concentration of the organic acid contained in the second organic layer.

Referring to Table 3, it was confirmed that Examples 4, 5, 8 to 10, which additionally performed the step of removing the alcohol after the first extraction and before the second extraction, not only had a second extraction efficiency of about 1.8 times higher than that of Comparative Example 2, but also had a distribution coefficient of about 4 times higher than that of Comparative Example 2 in the purification of the aqueous solution of 3-hydroxypropionic acid.

Experimental Example 4

Example 11

An aqueous solution containing 7.2 wt % of lactic acid was prepared as an aqueous solution of organic acids. For extraction, tri-n-octylamine was used as amine and 1-hexanol was used as alcohol.

After adding the alcohol and amine shown in Table 4 to the aqueous solution of organic acids and stirring at 20° C. for 17 hours, it was allowed to stand and separated into a first organic layer and a first aqueous solution layer to perform a first extraction.

Then, the content of the organic acid contained in the separated first organic layer was analyzed using HPLC, and the result is shown in Table 4 below.

TABLE 4

| | Aqueous solution of organic acids (g) | Solvent | | | | Aqueous solution of organic acids:solvent (volume ratio) | Reaction temp. (° C.) | Stirring time (hr) | 1st extraction efficiency (%) |
|---|---|---|---|---|---|---|---|---|---|
| | | Amine | | Alcohol | | | | | |
| | | Type | Amount (g) | Type | Amount (g) | | | | |
| Example 11 | 82.2 | TOA | 30.0 | Hexanol | 37.1 | 1:1.0 | 20 | 17 | 97.7 |

Experimental Example 5

Example 11

After the first extraction of the above Example 11, 1-hexanol in the first organic layer was removed by vacuum distillation at 70° C., and water was added to the first organic layer from which the alcohol was removed, followed by stirring at 90° C. for 7 hours. Then, it was allowed to stand and separated into a second organic layer and a second aqueous solution layer to perform a second extraction.

Then, the content of the organic acid contained in the separated second aqueous solution layer was measured using HPLC to analyze the extraction efficiency of the second extraction step, and the result is shown in Table 5 below.

Comparative Example 3

The first extraction was performed in the same manner as in the first extraction of Example 11. Thereafter, water was added to the first organic layer from which the alcohol was not removed, followed by stirring at 90° C. for 7 hours. Then, it was allowed to stand and separated into a second organic layer and a second aqueous solution layer to perform a second extraction.

Then, the content of the organic acid contained in the separated second aqueous solution layer was measured using HPLC to analyze the extraction efficiency of the second extraction step, and the result is shown in Table 5 below.

TABLE 5

| | 1st extraction | | | | 2nd extraction | | | |
|---|---|---|---|---|---|---|---|---|
| | Aqueous solution of organic acids (g) | TOA (g) | Hexanol (g) | Removal of alcohol | 2nd organic layer (g) | 2nd aqueous solution layer (g) | 2nd extraction efficiency (%) | Partition coefficient |
| Example 11 | 82.2 | 30.0 | 37.1 | ○ | 38.0 | 19.0 | 12.4 | 0.352 |
| Comp. Example 3 | 82.2 | 30.0 | 37.1 | X | 75.6 | 37.8 | 5.5 | 0.120 |

Referring to Table 5, it was confirmed that Example 11, which additionally performed the step of removing the alcohol after the first extraction and before the second extraction, not only had a second extraction efficiency of about 2.2 times higher than that of Comparative Example 3, but also had a distribution coefficient of about 2.9 times higher than that of Comparative Example 3 in the purification of the aqueous solution of lactic acid.

Thus, it was confirmed that the removal of the alcohol before the second extraction changed the state of the stable complex to increase the second extraction efficiency, thereby effectively obtaining the organic acid at a high concentration.

The invention claimed is:

1. A method for purifying organic acids, comprising:
   a first extraction, comprising separating an aqueous solution of organic acids into a first organic layer and a first aqueous solution layer by adding a solvent containing an amine and an alcohol;
   removing the alcohol from the separated first organic layer; and
   a second extraction, comprising separating the first organic layer from which the alcohol has been removed into a second organic layer and a second aqueous solution layer by adding water.

2. The method of claim 1, wherein the aqueous solution of organic acids is a fermentation broth obtained in a microorganism-based fermentation process.

3. The method of claim 1, wherein the aqueous solution of organic acids comprises an organic acid having 2 to 10 carbon atoms containing a hydroxy group.

4. The method of claim 3, wherein the aqueous solution of organic acids comprises an organic acid having 2 to 10 carbon atoms containing a hydroxy group at a concentration of 3 to 10%.

5. The method of claim 3, wherein the aqueous solution of organic acids comprises at least one organic acid selected from the group consisting of glycolic acid, 3-hydroxypropionic acid, lactic acid and 10-hydroxydecanoic acid.

6. The method of claim 1, wherein a volume ratio of the aqueous solution of organic acids and the solvent containing the amine and the alcohol is 1:0.5 to 1:1.5 in the first extraction.

7. The method of claim 1, wherein a weight ratio of the amine and the alcohol in the solvent is 15:85 to 45:55 in the first extraction.

8. The method of claim 1, wherein the amine comprises at least one amine selected from the group consisting of tri-n-octylamine, tridecylamine, and Aliquat 336.

9. The method of claim 1, wherein the alcohol comprises at least one alcohol selected from the group consisting of 1-hexanol, 1-heptanol, and 1-octanol.

10. The method of claim 1, wherein the first extraction is carried out at a temperature of 0 to 50° C.

11. The method of claim 1, wherein removing the alcohol from the separated first organic layer comprises removing the alcohol in the first organic layer by vacuum distillation.

12. The method of claim 1, wherein the second extraction is carried out at a temperature of 50 to 100° C.

\* \* \* \* \*